(12) United States Patent
Tsai

(10) Patent No.: US 11,879,842 B2
(45) Date of Patent: Jan. 23, 2024

(54) LUMINESCENCE IMAGING FOR GEMSTONE SCREENING

(71) Applicant: Gemological Institute of America, Inc. (GIA), Carlsbad, CA (US)

(72) Inventor: Tsung-Han Tsai, Maywood, NJ (US)

(73) Assignee: Gemological Institute of America, Inc. (GIA), Carlsbad, CA (US)

( * ) Notice: Subject to any disclaimer, the term of this patent is extended or adjusted under 35 U.S.C. 154(b) by 93 days.

(21) Appl. No.: 17/332,513

(22) Filed: May 27, 2021

(65) Prior Publication Data

US 2021/0389247 A1   Dec. 16, 2021

Related U.S. Application Data

(60) Provisional application No. 63/037,497, filed on Jun. 10, 2020.

(51) Int. Cl.
| | | |
|---|---|---|
| *G01N 21/64* | (2006.01) | |
| *G01N 33/38* | (2006.01) | |
| *G02B 27/14* | (2006.01) | |
| *G06T 7/90* | (2017.01) | |
| *G02B 27/10* | (2006.01) | |

(52) U.S. Cl.
CPC ....... *G01N 21/6456* (2013.01); *G01N 33/381* (2013.01); *G02B 27/1013* (2013.01); *G02B 27/141* (2013.01); *G02B 27/145* (2013.01); *G06T 7/90* (2017.01); *G01N 2201/061* (2013.01); *G01N 2201/062* (2013.01); *G06T 2207/10024* (2013.01); *G06T 2207/10064* (2013.01)

(58) Field of Classification Search
CPC ............ G01N 21/6456; G01N 33/381; G01N 2201/061; G01N 2201/062; G01N 21/87; G01N 21/6408; G01N 2021/6419; G02B 27/1013; G02B 27/141; G02B 27/145; G06T 2207/10024; G06T 2207/10064; G06T 2207/10152; G06T 7/0004

See application file for complete search history.

(56) References Cited

U.S. PATENT DOCUMENTS

| | | |
|---|---|---|
| 5,883,389 A | 3/1999 | Spear et al. |
| 6,020,954 A | 2/2000 | Aggarwal |
| 6,473,164 B1 | 10/2002 | De Jong et al. |

(Continued)

FOREIGN PATENT DOCUMENTS

| | | |
|---|---|---|
| CN | 209342610 U | 9/2019 |
| TW | 548401 B | 8/2003 |

(Continued)

*Primary Examiner* — David P Porta
*Assistant Examiner* — Mamadou Faye
(74) *Attorney, Agent, or Firm* — DLA Piper LLP (US)

(57) ABSTRACT

Systems and methods here may be used for a setup of image capturing of a gemstone, such as a diamond, exposed to different light sources. Some examples utilize a setup that both sends light and captures the image through multiple dichroic beam splitters at pre-selected timing. The multiple light source and multiple dichroic beam splitter arrangement allows for multiple gemstones to be analyzed using multiple methods with minimal moving, changing, or adjusting the equipment for different samples.

28 Claims, 8 Drawing Sheets
(3 of 8 Drawing Sheet(s) Filed in Color)

(56) References Cited

U.S. PATENT DOCUMENTS

| | | |
|---|---|---|
| 7,102,742 B2 | 9/2006 | Geurts |
| 9,678,018 B2 | 6/2017 | Takahashi |
| 10,107,757 B2 | 10/2018 | Takahashi |
| 10,684,230 B2 | 6/2020 | Wang et al. |
| 2010/0330578 A1 | 12/2010 | Duhr et al. |
| 2016/0290925 A1* | 10/2016 | Takahashi .............. G01N 21/87 |
| 2018/0003633 A1 | 1/2018 | Song |
| 2018/0195970 A1* | 7/2018 | Smith .................... G01N 21/64 |
| 2019/0337021 A1 | 11/2019 | Smith |
| 2020/0094289 A1 | 3/2020 | Portsmouth et al. |
| 2021/0310950 A1* | 10/2021 | Cheng ................. G01N 33/381 |

FOREIGN PATENT DOCUMENTS

| | | |
|---|---|---|
| WO | WO2017001835 A1 | 1/2017 |
| WO | 2019/185993 A1 | 10/2019 |
| WO | WO2020025031 A1 | 2/2020 |

\* cited by examiner

LUMINESCENCE IMAGING FOR GEMSTONE SCREENING

CROSS REFERENCE TO RELATED APPLICATION

The application relates to and claims priority from U.S. Provisional Application No. 63/037,497 filed on Jun. 10, 2020, the entirety of which is hereby incorporated by reference.

FIELD

The field includes utilizing various light sources and image capture for analyzing a diamond or other gemstone.

BACKGROUND

Lab-grown diamond and diamond simulants may possess different luminescence features compared with natural diamonds. Conventionally, gemologists evaluate those features under fluorescent lamps with ultraviolet emission by their eyes. Such observation entails using a dark environment because the luminescence features are usually faint, and ambient light may interfere or even overwhelm those features. Unfortunately, using the conventional protocol to screen diamonds is not practical due to the limitations in accuracy, reproducibility, and speed. Since human vision is good at detecting minor differences between samples but poor in quantifying the color and brightness, to accurately record the luminescence color and brightness is very difficult. After observation, to localize and label tiny samples from confirmed natural diamonds in a dark environment could also be very challenging. Human operators may also have to repeat the process multiple times to confidently localize all the samples. These limitations restrict the applications of using the luminescence features to reliably screening nature diamond from lab-grown diamond and diamond simulants.

The need for a systematic and easily reproducible analyzing method for gemstones is therefore needed. The value of a gemstone may rely on the analysis of whether it is actually a gemstone, which gemstone, and whether it was lab made or natural. As one single test may not be able to allow a human analyzer or computer to make all of these determinations, a set of tests may be necessary to make the best and most supportable determination. In the current analysis environment, there does not exist a single setup or system that can allow for many multiple tests to be performed, let alone on more than one gemstone at a time, in order to make determinations of natural or synthetic, and makeup of a gemstone under analysis. Further, it may be difficult to examine both loose gemstones and mounted gemstones. Systems and methods here address these shortcomings.

SUMMARY

Systems and methods here may be used to provide a method to analyze one or multiple gemstones, using multiple light sources, to analyze gemstones in an easily reproducible arrangement and produces reliable results.

Systems and methods of capturing and analyzing luminescence images of a sample gemstone described here include generating a first luminescence exciting beam at a first light source, directing the first luminescence exciting beam through a first filter and to a first dichroic beam splitter, and a second dichroic beam splitter, in some examples, alone or in combination, the first dichroic beam splitter is configured to reflect wavelengths of the first luminescence exciting beam and pass wavelengths of luminescence excitation from the sample gemstone, and in some examples, alone or in combination, the second dichroic beam splitter is configured to pass wavelengths of the first luminescence exciting beam, receiving, at a camera with a computer processor and a memory, a first excited luminescence image from the sample gemstone on a stage, wherein the excited first luminescence image having passed through the first dichroic beam splitter and the second dichroic beam splitter, generating a second luminescence exciting beam at a second light source, directing the second luminescence exciting beam through a second filter and to the second dichroic beam splitter, in some examples, alone or in combination, the second dichroic beam splitter is further configured to reflect wavelengths of the second luminescence exciting beam and pass wavelengths of luminescence excitation from the sample gemstone, receiving, at a camera with a computer processor and a memory, a second excited luminescence image from the sample gemstone on a stage, wherein the excited second luminescence image having passed through the second dichroic beam splitter and the first dichroic beam splitter, digitizing, by the camera computer, the received first and second luminescence images of the sample gemstone, and sending, by the camera computer, the digitized images of the sample gemstone table to a computer data storage. In some examples, alone or in combination, the generating the first luminescence exciting beam at a first light source is triggered by a computer in communication with the first light source, second light source, and camera. In some examples, alone or in combination, the first light source and the second light source are each one of longwave UV light, shortwave UV light, or broadband UV light. In some examples, alone or in combination, the digitized images are one of, a white light image, and a fluorescence excited by longwave UV light. In some examples, alone or in combination, the digitized images are one of, a fluorescence excited by two different shortwave UV light, and a phosphorescence from UV light.

In some examples, alone or in combination, systems and methods may also include analyzing, by a back end computer with a processor and a memory, the stored digitized image for determination of whether the sample gemstone is a natural diamond, synthetic diamond, or not a diamond. In some examples, alone or in combination, the dichroic beam splitter is configured to reflect wavelengths of the first light source and pass wavelengths greater than 400 nm. In some examples, alone or in combination, by the computer, based on the digitized images, defining color, brightness, and decay of different luminescence features. In some examples, alone or in combination, by the computer, using on the digitized images, distinguishing natural diamonds from synthetic diamonds and diamond simulants based on color, brightness, and decay.

Systems and methods for gemstone analysis here may include an optical layout with two light sources, wherein the light sources are both configured to illuminate a stage, in some examples, alone or in combination, the two light sources are different wavelengths, a top viewing camera in the optical layout configured to capture images of luminescence features in a gemstone under analysis on the stage, in some examples, alone or in combination, the camera is configured to view the stage through a first dichroic beam splitter where the first light source is aimed, and a second dichroic beam splitter where the second light source is aimed, a computer in communication with the at least two light sources and camera, wherein the camera is configured to use pre-defined integration time and camera gain to capture images of the gemstone under analysis on the stage. In some examples, alone or in combination, the two different light sources are at least one of a ultraviolet UV light emitting diode LED, laser, a laser driven light source LDLS, and a Xenon flash lamp. In some examples, alone or in combination, the computer is further configured to use an external trigger delay of the computer, or an internal trigger delay of the camera to capture images of phosphorescence luminescence features in a gemstone under analysis after the light source is off at different delay time. In some examples, alone or in combination, the digitized images are one of, a white light image, and a fluorescence excited by longwave UV light. In some examples, alone or in combination, the digitized images are one of a fluorescence excited by two different shortwave UV light, and a phosphorescence from UV light. In some examples, alone or in combination, the first light source and the second light source are each one of a longwave UV light, shortwave UV light, or broadband UV light. In some examples, alone or in combination, the computer is further configured, based on the digitized images, configured to define color, brightness, and decay of different luminescence features. In some examples, alone or in combination, the computer is further configured, to use the digitized images, to distinguish natural diamonds from synthetic diamonds and diamond simulants based on color, brightness, and decay. In some examples, alone or in combination, the second dichroic beam splitter reflection/transmission cutoff value is shorter than the first Dichroic beam splitter reflection/transmission cutoff value.

Systems and methods here for analyzing a gemstone may include illuminating, by a first light source, a gemstone on a stage, wherein the first illumination is aimed at a first dichroic beam splitter, configured to reflect radiation from the first light source through a second dichroic beam splitter to the gemstone on the stage, receiving, by a camera, aimed through the first dichroic beam splitter and the second dichroic beam splitter to the gemstone on the stage, a first set of images, illuminating, by a second light source, the gemstone on a stage, wherein the second light source is aimed at a second dichroic beam splitter configured to reflect radiation from the second light source to the gemstone on the stage, receiving, by the camera, aimed through the first dichroic beam splitter and the second dichoric beam splitter to the gemstone on the stage, a second set of images. In some examples, alone or in combination, the first illumination is between 365 nm to 400 nm in wavelength. 385 nm in wavelength. In some examples, alone or in combination, the first light source is an ultra-violet (UV) color light emitting diode (LED) with a band pass filter, and wherein the first set of images includes color and brightness of a gemstone fluorescence response under longwave UV light. In some examples, alone or in combination, the first set of images includes three images captured under illumination integration times between 0.5 and 200 ms. In some examples, alone or in combination, the second light source is a xenon flash lamp with a filter and wherein the second set of images includes color and brightness of a gemstone fluorescence response under shortwave UV light. In some examples, alone or in combination, the filter filters wavelengths of 227 nm or less. In some examples, alone or in combination, the second set of images includes three images captured under illumination integration times of 50, 200 and 500 ms. In some examples, alone or in combination, the second light source is a xenon flash lamp with a 239 nm filter and wherein the second set of images includes color and brightness of a gemstone fluorescence response under another UV wavelength. In some examples, alone or in combination, the second set of images includes three images captured under illumination integration times of 50, 200 and 500 ms. In some examples, alone or in combination, systems and methods include illuminating, by the second light source, the gemstone on a stage, wherein the second light source is aimed at a second dichroic beam splitter configured to reflect radiation from the second light source to the gemstone on the stage, receiving, by the camera, aimed through the first dichroic beam splitter and the second dichoric beam splitter to the gemstone on the stage, a third set of images. In some examples, alone or in combination, the second light source is a pulsing broad band xenon flash lamp and wherein the third set of images includes consecutively captured phosphorescence images of a gemstone under shortwave UV light. In some examples, alone or in combination, the camera captures images with 50 ms measurements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the embodiments described in this application, reference should be made to the Detailed Description below, in conjunction with the following drawings in which like reference numerals refer to corresponding parts throughout the figures.

DETAILED DESCRIPTION

Figure 1:
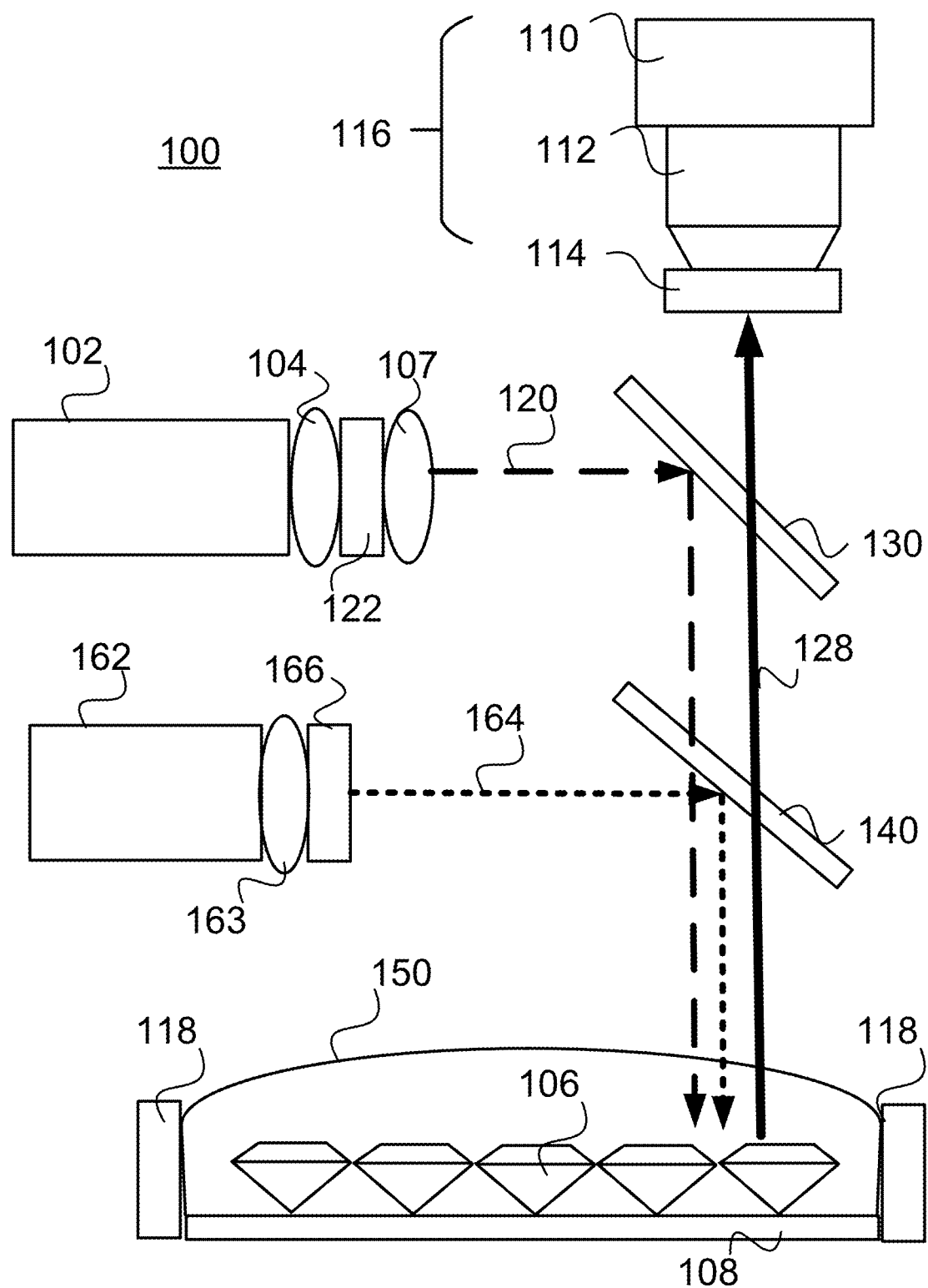
FIG. 1 is an illustration of an example analysis system in accordance with certain aspects described herein.

Reference will now be made in detail to embodiments, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular embodiments described herein are provided by way of example and should not be used to limit the scope of the particular embodiments. In other instances, well-known data structures, timing protocols, software operations, procedures, and components have not been described in detail so as not to unnecessarily obscure aspects of the embodiments herein.

Overview

In some examples, more than one test may be required to determine whether a gemstone is made of the material it is purported to be made of, is synthetic and made in a lab, and/or is natural and mined from the earth. For example, a naturally made diamond may be detected 84% of the time using a long wave UV fluorescence wavelength, and 14% of the time based on a short wave UV fluorescence wavelength. Even after this analysis around 2% of natural diamonds will not be properly detected.

Systems and methods here may be used for image capturing of many various gemstones, such as a diamond placed on a table, holder, and/or stage. Some examples utilize a single setup that is equipped with all of the light sources, lenses, cameras, filters, and gemstone stages to both generate and direct light and capture images of the gemstones by passing different light wavelengths from different light sources off dichroic beam splitters to the gemstone and capturing the reflected image for analysis through the same dichroic beam splitters. The multiple dichroic beam splitter arrangement allows for multiple light sources to be utilized while the same camera may view multiple gemstones with minimal moving, changing, or adjusting the camera equipment for many multiple different samples. Further, the dichroic beam splitter arrangement may create homogenous illumination environments for analysis.

Various methods may be employed using the setup, or similar, as described herein to accomplish different goals. One example method may use the setup described here to screen target gemstones such as diamonds to determine whether the diamond is synthetic. Another example method may use the setup described here to analyze the captured digitized pixelated images of gemstones. Such analysis may be used to detect diamond overgrowth on a natural diamond and detecting the absence of such overgrowth on a synthetic diamond. In such examples, the color of the fluorescence image may be used to detect overgrowth. For example, a diamond layer grown in a lab may generate a red color fluorescence instead of blue from a natural diamond. Also, such a layer may block the growth pattern of the natural diamond portion. Computer algorithms may be employed for such pixel analysis of the digitized images. Such analysis may also include comparison analysis between saved images and newly captured images. Any combination of the above, or any other analysis described herein may be combined into a single hardware arrangement as described.

Luminescence Examples

Systems and methods here may be used to first automatically localize gemstone samples within the field of view of the imaging system, and then capture and analyze fluorescence and phosphorescence color and brightness of the samples under different excitation wavelengths. The system may combine luminescence features from different lighting conditions to determine whether each individual sample is a natural diamond or not.

A white color visible light, such as a white color Light Emitting Diode (LED) may be used to generate the image for sample localization as well as to identify the boundary of the color analysis for each sample. In order to avoid strong reflection speckles and better represent the outline of the gemstone samples, a light diffuser may be used between the light source and the sample to create a homogeneous illumination around the samples. In some examples, shallow light incident angle may be used to reduce direct reflection to the camera.

The methods here may be used to measure gemstone samples under any number of excitation wavelengths, for example, under at least three different excitation wavelengths separately to collect the corresponding luminescence features, as described. The imaging system may detect these luminescence features during or after the excitation, any may utilize timing of the lights and camera as needed.

Fluorescence is one type of luminescence where the light emission may stop immediately after terminating the exposure. To capture the fluorescence, a sample may be illuminated by the light source where its wavelength is overlapped with one of a known absorption band of the sample. Since fluorescence may have a short timescale emission which decays nanoseconds after the excitation, the sample may need to be constantly illuminated to overserve its fluorescence signal. In order to prevent the excitation light from entering into the camera detector and overwhelming the emission, optical filters may be used to block the excitation light and/or to only allow the fluorescence signal to enter to the detector.

Phosphorescence is another type of luminescence where the emission may remain even after terminating the exposure. To capture phosphorescence, the samples may first be illuminated by the light, and the camera sensor starts to collect emission light immediately after terminating the exposure to isolate phosphorescence from the excitation light and the fluorescence signal. One consideration of phosphorescence is its speed/rate of signal degrade. One way to monitor this feature is to collect consecutive measurements after the light source is completely off and compare the brightness ratio between different frames.

Under each excitation wavelength, multiple camera settings such as integration time, gain or camera delays may be used to capture the representative luminescence color. The color information may be converted to hue, saturation, and/or lightness. The brightness may be calculated by the combination of the lightness from the color analysis, integration time of the camera, and/or the camera delay. The color and the brightness data may be analyzed to classify luminescence features.

Hardware Setup Examples

Figure 2:
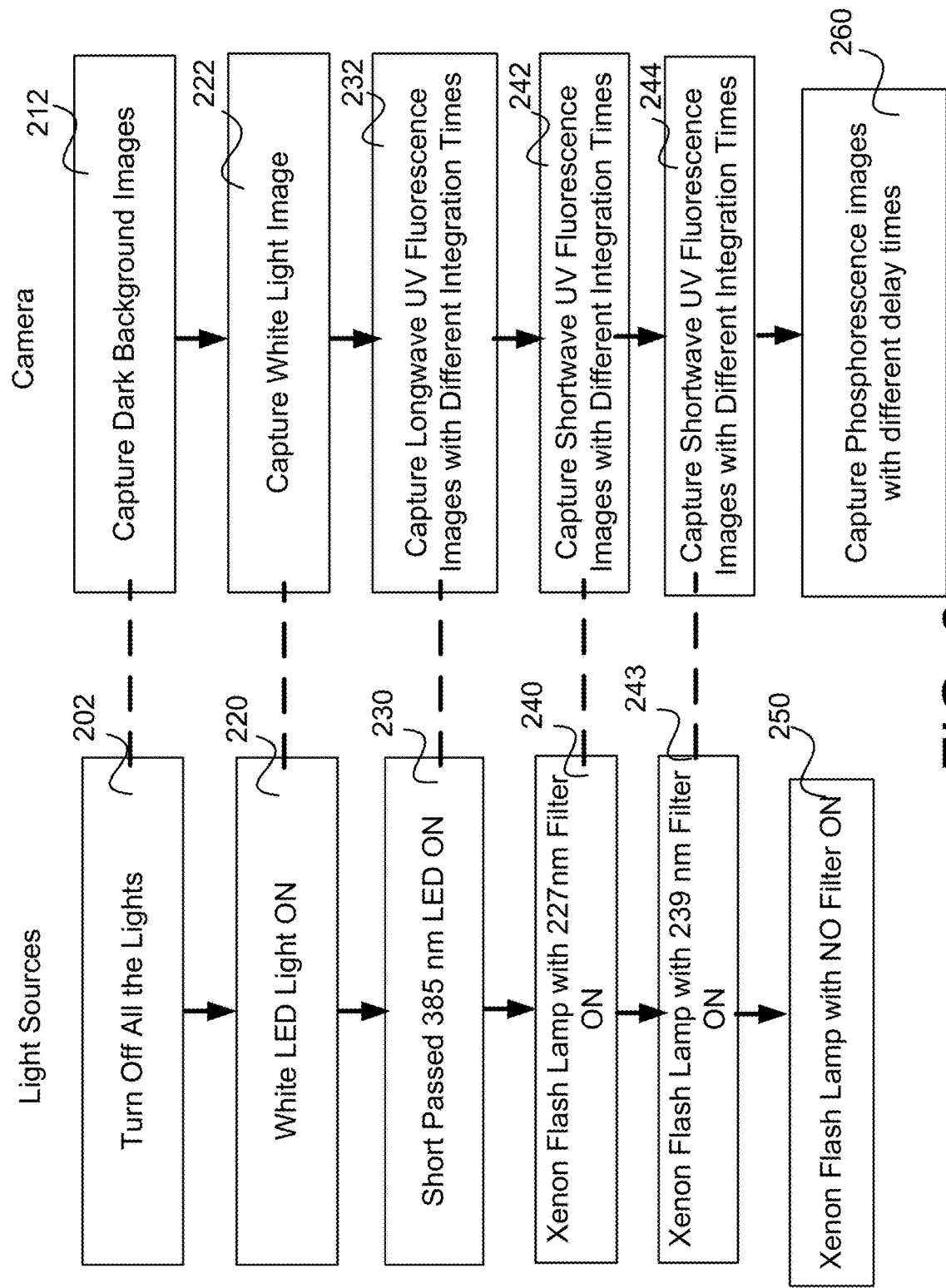
FIG. 2 is an illustration of an example flow diagram in accordance with certain aspects described herein.

FIG. 1 shows an example hardware setup 100 of the equipment which may be utilized to employ the methods described in FIG. 2 or otherwise herein using a color imaging camera with an imaging lens to collect gemstone luminescence signals. In the example, many multiple component parts may be included into one overall unit. This unit may include both camera arrangements 116, multiple light source arrangements 102, 162, 118, a gemstone stage 108 and the corresponding filters and lenses as described herein. All of this may have component parts in communication with a computer such as that described in FIG. 8 but not shown in FIG. 1. In this way, a single system may house and be able to adjust and command image capture and lighting as well as light timing and image capture timing as described herein to more efficiently capture gemstones 106 under various lighting conditions that may be useful in analyzing the gemstones 106 as described herein.

As shown in FIG. 1, the focal point for the emitted beams 120, 164, is the gemstone(s) 106 arranged in/on the stage 108. The operator may simply place any number of sample gemstones 106 in holders or on the stage 108 for analysis, and then move the table stage 108 and/or the rest of the system 100 to view the gemstones 106 that may be arranged on or in the stage 108. In some examples, stage 108 is a translation stage with the capability of three dimensional, X, Y, Z movement, and/or rotational movement using any of various motors either controlled manually or in communication with a computing system. The arrangement in FIG. 1 may allow for quick and easy analysis of many multiple samples and greatly simplifies the process for the operator, who otherwise would have to load a new gemstone 106 for analysis one at a time, of each different stone sample.

In order to guide the excitation wavelength to homogeneously illuminate the sample, two dichroic beam splitters 130, 140 have been used in the system examples. One advantage of using a dichroic beam splitter in the system described here is that the overall system may be more compact than if such an arrangement were not used. The use of the dichroic beam splitter allows for the inbound light beam(s) 120, 164 to the gemstone stage 108 and the images 128 from the gemstone stage 108 to pass through the same component part 130, 140 which minimizes the amount of space that such an arrangement takes up on a laboratory workspace. Further, the arrangement eases the use by the operator who can manipulate, carry, maneuver, and/or rearrange a compact system more easily than a spread out one.

In the example, a camera 110 and imaging lens 112 are arranged. In some examples, the imaging lens 112 may be a fixed magnification imaging lens, a macro lens (for less distortion), a telecentric lens (for long working distance), a manually or motorized adjustable magnification imaging lens (for changing field of view). The imaging lens may also include manual or motorized focusing (like a digital single-lens reflex camera, DSLR).

In some examples, a filter 114 is arranged in front of the imaging lens 112. In some examples, the filter 114 is a fluorescence filter. Such a camera arrangement 116 may be housed in a single housing or structure with the other arranged features described herein. In some examples, this camera arrangement 116 may be adjustable to adjust focal length, it may be fixed, or removable from the overall system 100. In some examples, the camera arrangement 116 may be positioned to view a stage 108 platform, table, holder, or other gemstone 106 support. In some examples, a light source such as LED panels 118 may surround, partially surround, approximate, be arranged under, and/or be arranged near the stage 108 so as to aid in illuminating the gemstones 106 which may be placed thereon or therein. In some examples, the stage 108 may include a transparent cover 150 made of glass, sapphire, quartz, or other material that may let light pass.

In some examples, the stage 108 may include a pre-arranged area to which the camera 116 field-of-view is set. In this pre-arranged area on the stage 108, the samples 106 for analysis may be placed, thereby being included in the camera 116 field-of-view.

In some examples, the camera arrangement 116 may be positioned such that the field of view includes the gemstone 106 stage 108 through a dichroic beam splitter 130. In some examples, two dichroic beam splitters 130, 140 may be arranged in sequence, such that the camera arrangement 116 is positioned so the field of view is through both dichroic beam splitters 130, 140 and then the stage 108. Any number of dichroic beam splitters, such as but not limited to one, two, three (not shown), four (not shown), five (not shown), six (not shown), or more may be similarly arranged. Such an arrangement may allow for the camera 116 to view the stage 108 and thereby any gems placed on or in the stage 108, through any number of dichroic beam splitters which may reflect different wavelengths of light toward the stage 108 as described herein.

A dichroic beam splitter 130, 140 may be used to reflect certain bands of light wavelengths and allow other bands of light wavelengths to pass. In such examples, the dichroic beam splitters may be arranged to reflect light from an equal number of light sources 102, 162. In such examples, light 120, 164 from the respective light sources 102, 162 may be generated and beams directed to reflect off the dichroic beam splitters 130, 140 and toward the gemstone 106 stage 108. In such a way, light from the different light sources may be reflected toward the stage 108 and thereby excite any gemstones 106 on the stage 108. In such an example, the excited light may travel back through the two dichroic beam splitters 130, 140 and to the camera 116 for imaging.

The dichroic beam splitter(s) 140, 130 may have different absorption coefficients for light polarized in different directions and may be used to selectively pass light of a small range of wavelengths while reflecting others. In some examples, the first splitter 130 may guide the longwave UV light to the sample, which reflect wavelengths below 395 nm and pass wavelengths above 400 nm. In some examples, the second splitter 140 may guide the shortwave UV light to the sample, which reflects wavelengths below 260 nm and pass wavelengths above 270 nm. In such examples, an average reflection ratio may be around 100:1, which may be enough to guide the excitation and relays the luminescence signal. In some examples, this reflected light may be between 400-700 nm in wavelength. Since the excited light from the gemstone 106, may be of a particular wavelength (between 400 nm-700 nm) it may pass through the dichroic beam splitter(s) 140, 130 instead of reflect off it as the original deep UV beam 120, 164 did.

In some examples, the dichroic beam splitter 130, 140 may reflect light with wavelengths less than 300 nm and allow light with wavelengths greater than 300 nm to pass. In some examples, the excitation wavelength is between 10 nm and 400 nm.

In some examples, the first light source 102 may be an ultra violet (UV) light emitting diode (LED) light source. In some examples, various filters and lenses may be arranged to focus the light generated by the light source 102 and directed toward the dichroic beam splitter 130. In some examples, a longwave UV filter 122 may be arranged after a first lens 104 and a second lens 107. In some examples, a single lens 104 may be used. In some examples, no separate lenses may be used.

In examples using two dichroic beam splitters, the relationship between two dichroic beam splitters may be coordinated. In such examples, reflection/transmission cutoff value of the lower Dichroic beam splitter 140 may be shorter than the upper Dichroic beam splitter 130.

In examples where the filter is specified, cutoff of lower Dichroic beam splitter 140 may be shorter than 350 nm. That means shorter than 350 nm will be reflected and longer than 350 nm will pass through. In some examples, a 325 nm cutoff may be used. In such examples, the first light source 102 LED may be between 350 nm and 410 nm. In some examples, a 385 nm light source may be used.

This design parallels the path of excitation wavelength and the luminescence signal, which can ignore the brightness deviation due to the angle between camera 110 and light sources 102, 162.

In examples using a light source filter 166, multiple different filters may be used. In such examples, one filter may be a 227 nm short pass filter, the other a 239 nm band pass filter. Any combination of these or other filters may be used. In some examples, a 227 nm filter may be replaced by any short pass or band pass filter that is shorter than 227 nm and blocking from 200 to 780 except the passing band. In some examples, a 239 nm filter may be replaced by and filter has passing band between 227 and 250 and blocking from 200 to 780 except the passing band.

In some examples, the second light source 162 may be a Xenon (Xe) flash lamp. In some examples, the second light source may be arranged with a filter 166 through which the beam 164 generated by the second light source 162 may be directed toward the dichroic beam splitter 140 and toward the gemstone 106 stage 108. In some examples, a lens 163 may be placed between the second light source 162 and the filter 166. In some examples, the filter 166 may be a removable shortwave UV, in some examples, it may be a 227 nm short pass filter, in some examples, it may be a 239 nm band pass filter, and in some examples, there may be no filter used.

It should be noted that a UV LED light source, an LED light source, and a Xenon flash lamp, and laser with wavelengths between 350 and 410 nm are not the only light sources that may be utilized. The example of a UV LED and a Xenon flash lamp are merely non-limiting examples. Other kinds of light sources may be arranged, in any number, and in any order, with corresponding dichroic beam splitters. In some examples, the light source 102 is a laser driven light source (LDLS). In some examples, the light source 102 may be a deuterium lamp. In some examples, the light source 102 may be a 224.3 nm HeAg laser. In some examples, an LDLS or the HeAg laser can replace the Xenon flash lamp 162 as the second light source.

In some examples, a computer system is in communication with the light systems. In such examples, the computer may control timing of energizing, or turning the light sources 102, 162 either on or off to direct different combinations of light at different times toward the stage 108 and thereby illuminate/excite the gemstones 106 which may be placed there. The camera 116 may then capture the excited light 128 emitted by the gemstones 106 which travels back through the two dichroic beam splitters 140, 130 toward the camera lens 112 and the image capturing camera 110.

No matter how many separate beams of light are directed toward the gemstone 106 stage 108, they may excite 128 and travel back up through the dichroic beam splitters 140, 130 of however many are arranged and through the filter 114 if there is one, camera lens 112 and image capture camera 110.

This allows the gemstone reflected beam 128 to continue the camera arrangement 116 and/or to an optional mirror (not pictured) and then to the camera arrangement 116. The camera lens 112 may help to narrow the beam spot of the reflected light 128 for better analysis. In some examples, the reflected light 128 could be any light which comes from the sample(s) 106, for example, reflected, transmitted, or emitted light. Under white light, 128 could be reflected or transmitted light. Under light sources 102 or 162 will be reflected, transmitted, and emitted light, but the reflected light from light sources 102 and 162 will be blocked by the filter 114 and or beam splitters. The camera 110 may be a light sensitivity color camera. In some example embodiments, an additional filter 114 may be placed before the lens 112 of the camera 110. In such examples, the additional filter 114 may enhance the contrast of the pattern or feature of a gemstone fluorescence image. The additional filter 114 may be any one of or combination of a long pass filter, a band-pass filter, a short-pass filter, and a polarization sensitive (combination of a polarizer and waveplate) filter.

Any number of filters 114, 122, 166 may be arranged on the system 100, in any combination and permutation. In some examples, the filters 114, 122, 166 may be any kind of filter including but not limited to a deep UV filter allowing only deep UV light to pass, in some examples, a polarization sensitive filter, a combination of a polarizer and a waveplate that enhance the contrast of the pattern or feature in a gemstone image.

To further isolate the reflected excitation signal from the luminescence signal, a long pass filter 114 may be placed in front of the imaging camera 110 to only allow wavelength longer than 410 nm to pass and then being collected by the imaging camera 110. In some examples, the filter 114 may be a removable shortwave UV filter to filter the light during the shortwave UV fluorescence measurement and removed during the phosphorescence measurement to increase the brightness of the phosphorescence signal.

Further, in some examples, the LED light panels 118 surrounding, or otherwise near the stage 108 may be utilized to illuminate the gemstones 106 as well. In some examples, 118 may be white light LED, which may covers from 400 nm to 700 nm wavelength. The color temperature of the white light LED could between 2,800K to 6,500 K, and in some examples, 5,000K. The Color Rendering Index (CRI) value could be from 80 to 98. In some examples, white LED with CRI >90 may be used.

This camera 110 may then digitally receive and/or capture the excited image of the gemstone(s) 106 for analysis as described herein. In such a way, the camera imaging system 110 sequentially may collect/capture a white light image, any longwave fluorescence images, any shortwave fluorescence images, and/or the phosphorescence images by automatically controlling the light sources 102, 162 and measuring the images under or after the excitation. The representative color and brightness may be calculated from the fluorescence and phosphorescence images as described herein. These luminescence features can be used together to screen synthetic diamonds and diamond simulants out from natural diamonds.

Such an image may include color pixelated data representing the gemstone fluorescence image as described herein. The camera 110 may include computer components, for example as described in FIG. 7 and FIG. 8 and may also be in communication with other computer components as described herein for timing the camera image capture, processing the pixelated digital images, for saving, storing, sending, and/or otherwise analyzing or manipulating the pixelated digital images of the gemstone tables.

Timing Examples

Figure 3:
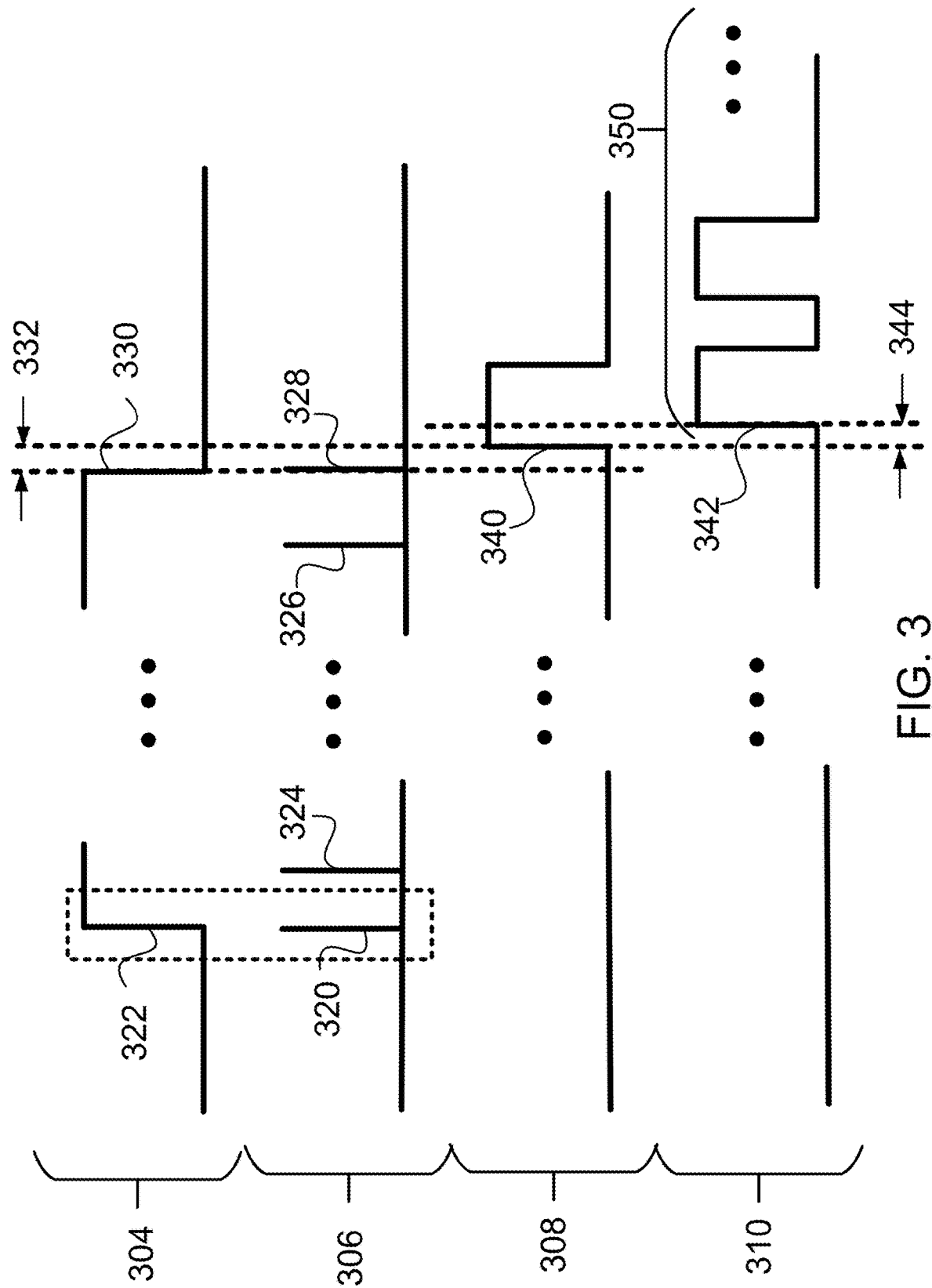
FIG. 3 is an illustration of an example timing diagram in accordance with certain aspects described herein.

Using the setup of FIG. 1, many various images of gemstones may be captured under many various light conditions at specific, pre-determined times. In some examples, the timing of these images capture and timing of the light illuminations may be orchestrated by a computer system program using various algorithms, programs, and/or instructions. FIG. 2 and FIG. 3 show examples of timing algorithms that may be used by the system and related computers to time the lighting and image captures.

For example, in some situations, analysis of gemstones may utilize directed radiation that excites the sample stone, and the result is that the stone exhibits a fluorescence, phosphorescence, or other visible or discernible characteristic. That excitation may change over time and may decay at a rate that depends on the amount and duration of the excitation radiation. As the analysis of the gemstone may be reliant on an image captured of the gemstone at its highest or as close to its highest point of excitation, yet not an image of the directed excitation radiation itself, the timing of both the excitation application and the camera image capture may affect the analysis. Timing of both the illumination and the camera image capture may therefore be determined and then applied to a sample for analysis.

In one such example, a UV light is applied to a sample stone, and when excited the stone begins to exhibit luminescence. The UV excitation light is not meant to be captured in the camera image because an analysis of the stone with the UV excitation light on may alter the analysis. Also, when the UV excitation light is turned off, the stone may emit a fluorescence but that fluorescence emission begins to decay over time as phosphorescence. Therefore, in different analysis examples, the image capture may be timed such that it does not directly capture the UV excitation light, but captures the stone exhibiting fluorescence at as high of a point as possible as it begins to decay after the UV excitation light is turned off. Also, various camera imaging equipment used in such examples may have their own lag times between being triggered and image capture. This timing and alignment of excitation illumination and image capture is described in more detail below.

In some examples, a representative color and brightness may be chosen from a series of measurements which within a certain signal range in order to avoid low signal to noise ratio signal or strong signal which saturates the sensor. Both too low and too strong signal may deviate the color values. The combination of lightness in the color analysis and the raw red, green, and blue pixel value from the camera may be used to select the representative color. The luminescence color may be calculated by averaging the color data in each sample after filtering out the obvious dust and inhomogeneous color elements.

The first excitation wavelength for luminescence measurement may be in the longwave UV range, optionally from 365 nm to 400 nm and in some examples, 385 nm. The light source may be an ultra-violet (UV) color LED which using band pass filter to block the visible light component and using lenses to control the beam spot. The camera may be used to capture several images with different integration time settings during the UV light exposure in order to cover gemstones with luminescence signal from faint to very strong. For example, five different integration times, such as 0.5, 2, 10, 50, and 200 ms could be used. In some examples, integration times ranging from 0.5 ms to 200 ms may be used. The color and brightness from the images may represent a fluorescence response of a gemstone under longwave UV light.

The second excitation wavelength may be in the shortwave UV range from 200 nm to 230 nm. The light source may be a xenon flash lamp filtered by a band pass or short pass filter, optionally 227 nm or less. The camera may be used to capture several images with different integration time settings during the UV light exposure in order to cover gemstones with luminescence signal from faint to very strong. For example, three different integration times, such as 50, 200 and 500 ms could be used. In some examples, integration times from 50 to 500 ms may be used. The color and brightness from the images may represent a fluorescence response of a gemstone under shortwave UV light.

One optional excitation wavelength is in the shortwave UV range from 230 nm to 250 nm. The light source may be a xenon flash lamp filtered by a band pass filter, optionally 239 nm. The camera may be used to capture several images with different integration time settings during the UV light exposure in order to cover gemstones with luminescence signal from faint to very strong. For example, three different integration times, such as 50, 200 and 500 ms could be used. In some examples, The color and brightness from the images represent gemstone's fluorescence response under another shortwave UV light.

The last excitation wavelength may be a pulsed broad band light which includes shortwave UV components with wavelengths from, for example, 200 to 250 nm. The light source may be a xenon flash lamp or other light source. An electrical trigger signal generator may be used to accurately control the length which the light source is exciting the sample and the time when the camera starts to consecutively capture the phosphorescence images. In some examples, this trigger signal may come from a computerized program. The length of the light source may be selected to maximized the phosphorescence from high-temperature-high-pressure treated CVD lab-grown diamond and minimized the phosphorescence from high-temperature-high-pressure (HPHT) lab grown diamond. A fixed trigger delay time may be applied to the camera to start the consecutively measurements after the light source is completely off or unable to be detected by the camera. Each consecutive measurement may have the same integration time and gain setting. In one non-limiting example, an integration time may be 50 ms and the number of measurements may be three, four, or five. The proper color may be calculated from one of the consecutive images which meets the signal range requirement. The color and brightness from the images may represent the phosphorescence response. Finally, the ratio of brightness between different phosphorescence images may represent response time of the phosphorescence signal.

FIG. 2 depicts an example flow chart detailing examples of how the systems and methods described herein may capture gemstone images for analysis under varying light conditions, and after excitation by various illumination sources.

As can be seen in FIG. 2, the light source and camera may be synchronized such that the camera captures images at specific times when the light settings are predetermined to deliver a specific light environment for gemstone analysis, and/or excitation of the gemstone is able to be captured. In the example, the White light may be light with wavelengths between 400 and 700 nm, the Longwave UV LED light may be between 350 and 410 nm and the Xenon light may be between 200 and 900 nm. In some examples, the filter may filter light below/above 227 nm wavelength. In some examples, different light sources may be used in any combination here or otherwise, the examples of Xenon, LED and white LED are merely examples and not intended to be limiting.

In this example, first, Light Sources turn off all the lights 202 and the Camera captures dark background 212.

Next, the Light Sources turn White LED light ON 220 and the Camera captures White Light Image 222.

Next, the Light Sources turn Short Passed 385 nm LED light ON 230 and the Camera captures longwave UV fluorescence images with different integration times 232.

Next, the Light Sources turn Xenon Flash Lamp with 227 Filter ON 240 and the Camera captures shortwave UV fluorescence images with different integration times 242.

Next, the Light Sources turn Xenon Flash Lamp with 239 nm Filter ON 243 and the Camera captures shortwave UV fluorescence images with different integration times 244.

Next, the Light Sources turn Xenon Flash Lamp with no Filter ON 250.

FIG. 3 shows another example timing diagram with binary digital signals shown as communications between and among a computing system, a lighting system and a camera system. Due to the response time of a light emitter such as a Xenon flash lamp, in order to capture images with cameras at predetermined conditions, such as when the sample gemstone is exhibiting phosphorescence after being excited by the light source, computerized timing may be programmed into the system for both light on/off and camera capture and duration. In some examples, it may not be useful to capture an image of the sample gemstone while the illumination source is on, but rather, as close to the time the light source is off, so as not to capture the light source itself, but the excitation of the gemstone displaying phosphorescence emission. And as such phosphorescence may decay over time, the image capture may be timed for a specifically determined analysis. In some examples, every 10 ms (0.01 seconds) the trigger is set and it takes 20.6 µs for the lamp to fully energize and/or de-energize, and/or decay from a fully energized state to a fully de-energized state. Because of this lag time, various triggers and wait times may be programmed into the system to capture the images required for analysis.

Starting with one timing example 304, trigger one is a trigger signal from the computer system for the light source 306 to turn on. When the trigger one goes high 322, the light source 306 pulses ON 320. The light source then pulses on 324, 326, 328 for as long as the light source trigger 304 is high 322. The timing example may only be used in phosphorescence measurement (FIGS. 2, 250 and 260). The other fluorescence and white light measurements capture images while the light is on.

In some examples, the light source is on for approximately 500 milliseconds (ms). In some examples the time is approximately 50 pulses. In some examples, the light source is energized for 10 to 10,000 ms.

For the camera to capture an image in the correct conditions, with the excitation light off but the decay of the stone still high or as high as possible, the timing of the image capture may be aligned with the light source activation and deactivation as shown.

Thus, when trigger one, the trigger sent from the computer system to the light source, goes from high to low 330 to turn off the light source, and the last light source pulse 328 occurs, in some examples, a wait time of approximately 130 µs occurs 332 before the second trigger signal 340 is sent, the trigger from the computer system to the camera, 308 to the camera goes high 340. In some examples, the wait time may be programmed to be 130 µs. In some examples, the wait time may be programmed to be between 0 and 1000 µs. The response time for the camera 310 to respond 342 to the second trigger 308 signal going high 340 is around a few µs 344. Once on, the camera 310 captures images 350 with multiple consecutive 50 ms measurements. In some examples, the camera 310 captures images 350 with 50 ms measurements. In some examples, the camera 310 captures images 350 with between 1 to 1000 ms measurements. These captured phosphorescence images are then used in the analysis method steps described herein.

Hardware Calibration Examples

In some examples, it may be useful to calibrate the hardware disclosed herein. In such examples, all of the light sources 102 and 162 of FIG. 1 may be used to create beam spots which are equal to, or bigger than the field of view provided by the imaging system 116. The beam spot can be adjusted by moving the lenses 104, 107 or the position of the light sources 102, 162 closer or away from the gemstone samples 106 (the relative distance to the sample). If the field of view is smaller than the imaging system, only partial of the full field of view may be used. The imaging system may need to focus on the samples 106, or the sample image may need to be reasonably clear. If the sample is out of focus, the system may adjust the vertical (Z) position of the stage. Use samples with known luminescence features to calibrate the camera setting, including integration time, camera gain, and the initial trigger delay as described in 332 of FIG. 3.

Example Analysis Steps

Using the systems and methods here, once the images are captured as described, an analysis of them may be made to determine gemstone color which may include a conversion of R, G, B, to Hue, saturation and value for color analysis using the analysis steps described herein. In some examples, the pixelated images of the gemstones under different light conditions, exhibiting different excitation characteristics, captured by the camera may be analyzed, including analysis of hue, saturation, and/or lightness to make a color determination and/or thereby a determination of whether the gemstone is natural or not natural.

For example, the red (R), green (G), blue (B) values of each of the image pixels may be converted to Hue (on a scale from 0-360°); Saturation (on a scale from 0-100%); and Lightness (on a scale from 0-100%) also referred to as "HSL." In some examples, the detector saturation is R, G, B of 255 which should be avoided.

In some examples, when a pixel receives more than 255 counts of signal, it reaches its maximum value. In such a way, even receiving more signal does not increase the reading. Such a saturation situation may create a wrong color (hue, saturation and lightness).

Figure 4:
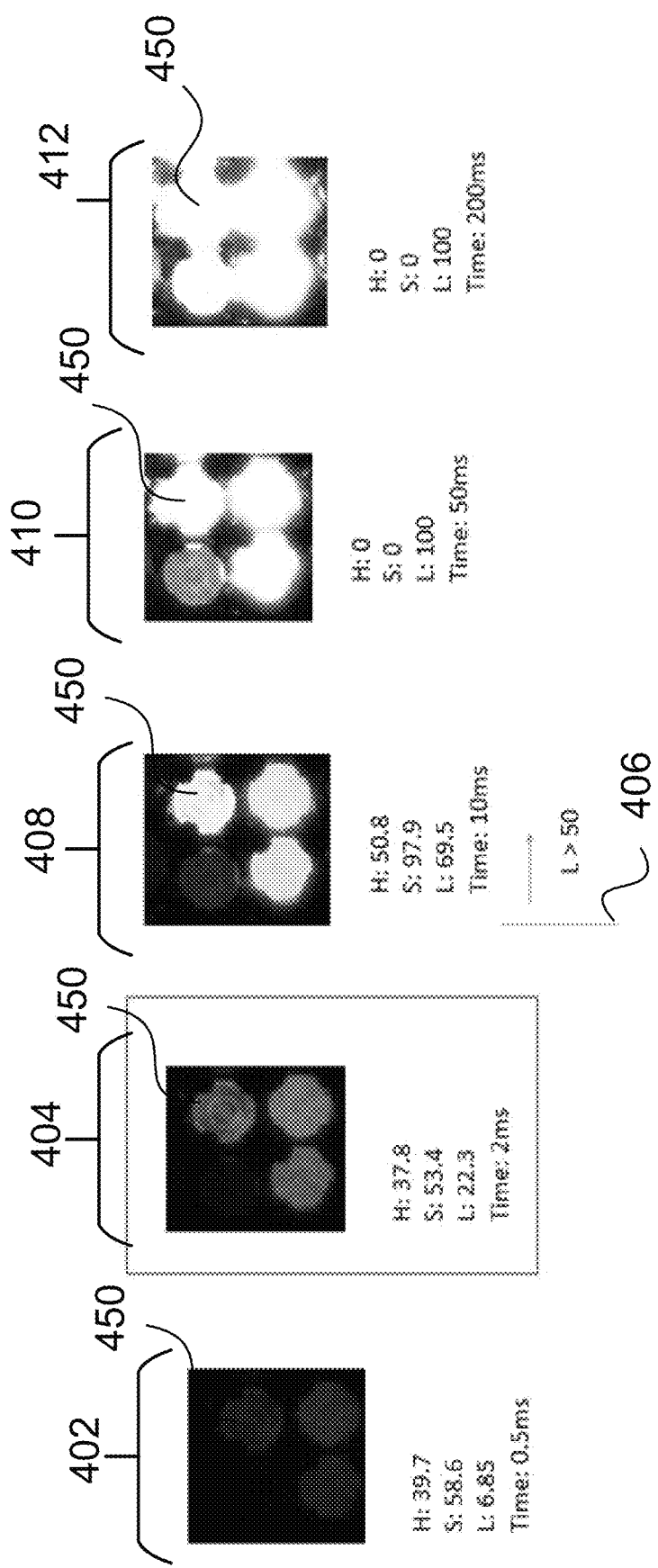
FIG. 4 is an example showing multiple illumination examples in accordance with certain aspects described herein.

For phosphorescence image captures, in some examples, a choice of images with proper integration time/camera delay may be utilized. In some examples, a threshold of lightness images may be set, such that any images below that predetermined threshold are considered as no signal and not utilized in the analysis. In some examples, the HSL values of phosphorescence and/or fluorescence may be utilized. In some examples, the analysis based on the HSL values and the corresponding integration time/camera delay, may be used to screen gemstones, determine whether they are natural or unnatural, and/or their color. FIG. 4 shows examples of the same grouping of stones with different HSL values taken from the top right sample 450 in the four samples shown, for example, 402 with an H: 39.7; S: 58.6; L: 6.85 Time 0.5 ms. For example, 404 with an H: 37.8; S: 53.4; L: 22.3 and Time: 2 ms. For example, 406 having a threshold of L>50 for example, 408 with an H: 50.8; S: 97.9; L: 69.5; and Time: 10 ms. For example, 410 with an H: 0; S: 0; L: 100; and Time: 50 ms. For example, 412 with an H: 0; S: 0; L: 100; and Time: 200 ms. Using this analysis, an L threshold value may be selected. In some examples, one of the stones in the sample may be prioritized, or analyzed to aid in the L threshold 406 selection.

For example, after all of the images are captured by the systems and methods described herein, the images may be analyzed in specific sequences to either pass them as natural gemstones, or refer them for more testing as potentially not natural gemstones. Image analysis of the pixelated digitized images may be made as comparisons against predetermined examples and/or thresholds which may serve as examples of the pass/fail criteria.

Below is one example protocol which can be used in the systems and methods here for analysis. In such examples, high pressure and high temperature (HPHT) processed chemical vapor deposition (CVD) synthetic diamond may have strong and fast degrading phosphorescence signal. The first frame of phosphorescence image may have medium level of "Lightness" value. The phosphorescence signal may degrades quickly, and may be undetectable in the fourth and the fifth frames. This type of samples has color close to yellowish green, where its Hue value is around 100.

CVD synthetic diamonds could show detectable and fast degrading phosphorescence signals. The signal may be weak in the first frame and undetectable in other frames. This type of samples has color close to orange red, where its Hue value is around 0.

Glass diamond simulant could show two types of phosphorescence signals. The first type may have very strong but fast degrading phosphorescence signal. The first frame of phosphorescence image may have very high "Lightness" value but it may become undetectable in other frames. This type of sample may have color close to aero blue, where its Hue value is close to 150. The other type of glass phosphorescence feature is similar to the CVD synthetic diamond.

Figure 5:
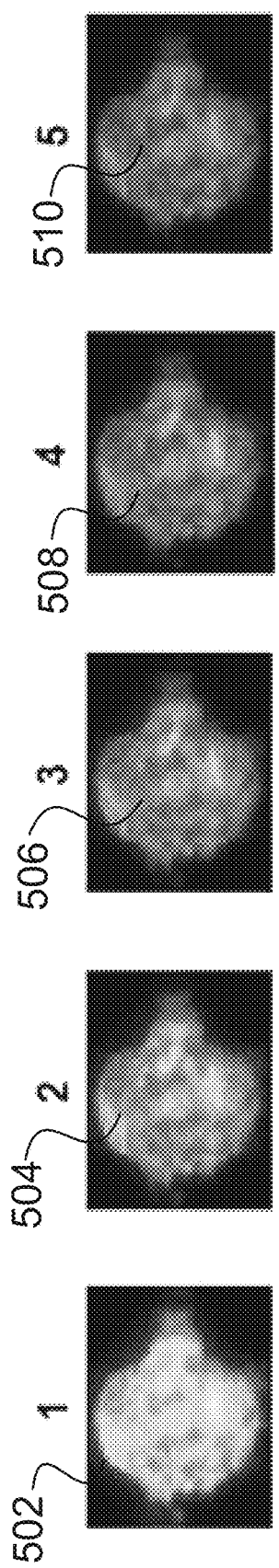
FIG. 5 is another example showing multiple illumination examples in accordance with certain aspects described herein.

FIG. 5 shows an example of phosphorescence image captures as described herein, showing examples where it may be required to refer suspicious phosphorescence results. In the example, HPHT synthetic diamond is shown. HPHT synthetic diamond has very strong and slow degrading phosphorescence signal. The first frame of phosphorescence image usually has very high "Lightness" value. Long lasting phosphorescence signal may be applied and the results are a high lightness in the first phosphorescence image 502, a little less in the next 504, a little less in the next 506, a little less in the next 508. Even the fifth frame phosphorescence image 510 could have reasonably high "Lightness" value. This type of samples has color close to aqua blue, where its Hue value is close to 180. Samples with suspicious shortwave UV excited fluorescence features should be referred for further testing.

HPHT processed CVD synthetic diamond may have medium brightness green color fluorescence signal under shortwave UV. The Hue value is around 100. CVD synthetic diamonds may have medium brightness orange color fluorescence signal under shortwave UV. The Hue value is around 30. Cubic Zirconia (CZ) may have weak brightness blue color fluorescence signal under shortwave UV. The signal may be stronger under 239 nm excitation than under 227 nm excitation. The Hue value may be around 210.

Third, samples with natural diamond longwave or short wave UV excited fluorescence features can be passed as natural diamond. Natural diamonds can show blue color fluorescence with Hue value close to 220 and "Saturation" value above 35. Some natural diamond may show strong yellow or white color fluorescence with Hue value between 35 and 325. The required integration time is usually equal or shorter than 50 ms. Some natural diamond may show very weak or off color fluorescence under longwave UV but detectable blue fluorescence under shortwave UV excitation. The Hue value may be between 190 and 230 with Saturation above 30. In some examples, samples which cannot be classified by one of the above groups should be referred for further testing.

Additional excitation wavelength could be added in order to better identify specific type of samples. For example, cubic zirconia shows stronger characteristic fluorescence under 240 nm excitation than under below 227 nm excitation, while diamonds with weak shortwave UV fluorescence may be inert to this wavelength and show no fluorescence.

The processing device of the imaging system may summarize the result by localizing the position of each gemstone samples automatically and decide whether the sample is a natural diamond or should be referred for advanced testing. The sample localization could also be achieved by the user through selecting or cropping the area of interested in white light image. The final result may be analyzed by a computer in communication with the camera system and may be displayed on a screen.

Figure 6:
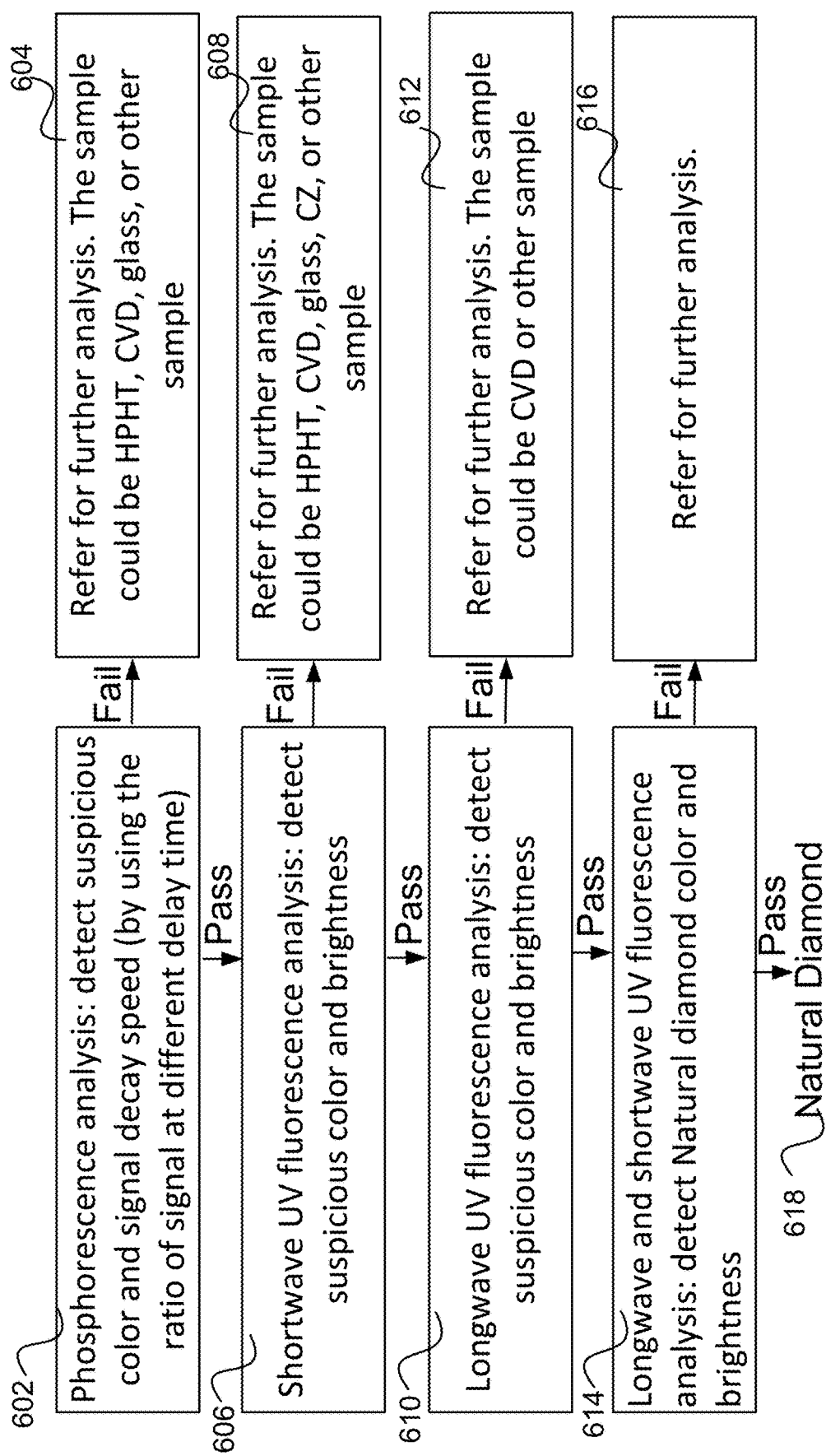
FIG. 6 is an illustration of another example flow diagram in accordance with certain aspects described herein.

FIG. 6 shows an example flow chart showing one such example set of method steps to make the natural determination. In the flow chart depicting the method steps, first 602 Phosphorescence analysis: detect suspicious color and signal decay speed (by using the ratio of signal at different delay time), if it fails, 604 refer for further analysis. The sample could be HPHT, CVD, glass, or other sample. If it passes, move to next step 606 Shortwave UV fluorescence analysis: detect suspicious color and brightness. If it fails, 608 refer for further analysis. The sample could be HPHT, CVD, glass, CZ, or other sample. If it passes, move to next step 610, Longwave UV fluorescence analysis: detect suspicious color and brightness. If it fails, 612 refer for further analysis. The sample could be CVD or other sample. If it passes, move to next step 614 Longwave and shortwave UV fluorescence analysis: detect Natural diamond color and brightness. If it fails, 616 refer for further analysis. If it passes, move to next step it is a natural diamond 618.

Network Examples

Figure 7:
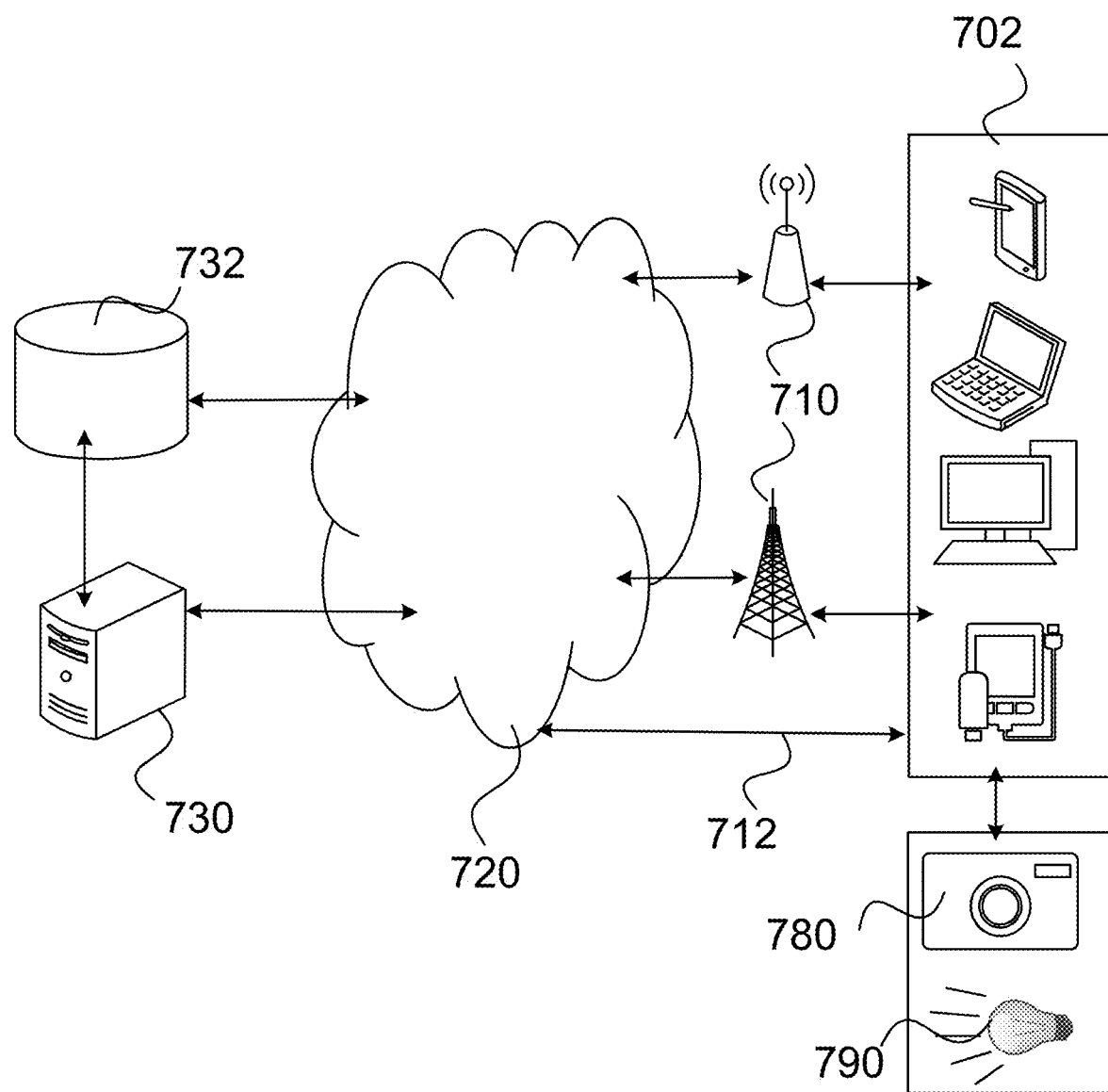
FIG. 7 is an illustration of an example networked system in accordance with certain aspects described herein.

An example of a networked computing arrangement which may be utilized here is shown in FIG. 7. In FIG. 7, the computer 702 used to process the image from the camera (142 in FIG. 1) may generate data which includes pixel data of the captured images. The computer 702 could be any number of kinds of computers alone or in combination such as those included with the camera itself, the light source itself, and/or another computer arrangement in communication with the camera and/or light computer components and in some examples, the stage motors and/or camera lens motors, including but not limited to a laptop, desktop, tablet, phablet, smartphone, or any other kind of device used to process and transmit digitized data. Such a computer 702 may be used to control a camera 780 and/or light generating device 790 as described herein. The computer 702, additional or alternative examples are described in FIG. 8.

Turning back to FIG. 7, computer resources for any aspect of the system may reside in networked or distributed format over the network 720. Further, the data captured for the pixelated image from whichever computer 702 may be transmitted to a back end computer 730 and associated data storage 732 for saving and analysis. In some examples, the transmission may be wireless 710 by a cellular or WiFi transmission with associated routers and hubs. In some examples, the transmission may be through a wired connection 712. In some examples, the transmission may be through a network such as the internet 720 to the back end server computer 730 and associated data storage 732. At the back end server computer 730 and associated data storage 732, the pixelated image data may be stored, analyzed, compared to previously stored image data for matching, or any other kind of image data analysis. In some examples, the storing, analyzing, and/or processing of image data may be accomplished at the computer 702 which is involved in the original image capture. In some examples, the data storing, analyzing, and/or processing may be split between the local computer 702 and a back end computing system 730. Networked computer resources 730 may allow for more data processing power to be utilized than may be otherwise available at the local computers 702. In such a way, the processing and/or storage of image data may be offloaded to compute resources that are available on the network. In some examples, the networked computer resources 730 may be virtual machines in a cloud infrastructure. In some examples, the networked computer resources 730 may be spread across many multiple computer resources by a cloud infrastructure. The example of a single computer server 730 is not intended to be limiting and is only one example of a compute resource that may be utilized by the systems and methods described herein.

Example Computer devices

As described, any number of computing devices may be arranged into or connected with the various component parts of the systems described herein. For example, the camera systems may include their own computing systems, the lighting systems may include their own computing systems, the data from the camera images may be collected, stored and analyzed using computing systems. Such systems may be local and in direct connection with the systems described herein, and in FIG. 7. In some examples, some of the computing resources may be networked, or in communication over a network, such that they are not necessarily co-located with the optics systems described herein. In any case, any of the computing systems used here may include component parts such as those described in FIG. 8.

Figure 8:
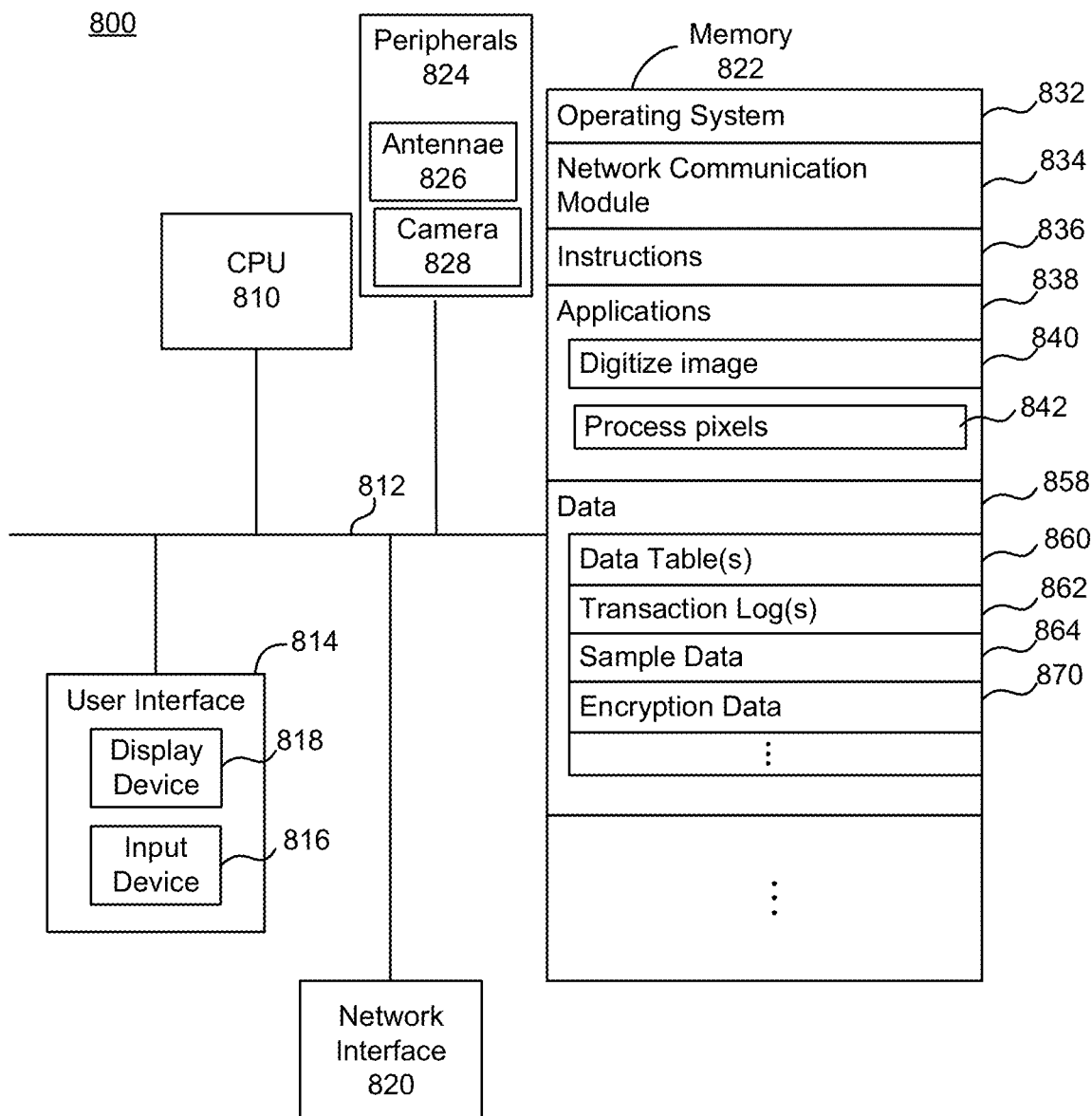
FIG. 8 is an illustration of an example computer system in accordance with certain aspects described herein.

FIG. 8 shows an example computing device 800 which may be used in the systems and methods described herein. In the example computer 800 a CPU or processor 810 is in communication by a bus or other communication 812 with a user interface 814. The user interface includes an example input device such as a keyboard, mouse, touchscreen, button, joystick, or other user input device(s). The user interface 814 also includes a display device 818 such as a screen. The computing device 800 shown in FIG. 8 also includes a network interface 820 which is in communication with the CPU 820 and other components. The network interface 820 may allow the computing device 800 to communicate with other computers, databases, networks, user devices, or any other computing capable devices. In some examples, the method of communication may be through WiFi, cellular, Bluetooth Low Energy, wired communication, or any other kind of communication. In some examples, the example computing device 800 includes peripherals 824 also in communication with the processor 810. In some examples, peripherals include antennae 826 used for communication. In some examples peripherals 824 may include camera equipment 828. In some example computing device 800 a memory 822 is in communication with the processor 810. In some examples, this memory 822 may include instructions to execute software such as an operating system 832, network communications module 834, other instructions 836, applications 838, applications to digitize images 840, applications to process image pixels 842, data storage 858, data such as data tables 860, transaction logs 862, sample data 864, encryption data 870 or any other kind of data.

Conclusion

As disclosed herein, features consistent with the present embodiments may be implemented via computer-hardware, software and/or firmware. For example, the systems and methods disclosed herein may be embodied in various forms including, for example, a data processor, such as a computer that also includes a database, digital electronic circuitry, firmware, software, computer networks, servers, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the embodiments or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the embodiments, or it may be more convenient to construct a specialized apparatus or system to perform the required methods and techniques.

Aspects of the method and system described herein, such as the logic, may be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, and so on).

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the descriptions have been specifically described herein, it will be apparent to those skilled in the art to which the descriptions pertains that variations and modifications of the various implementations shown and described herein may be made without departing from the spirit and scope of the embodiments. Accordingly, it is intended that the embodiments be limited only to the extent required by the applicable rules of law.

The present embodiments can be embodied in the form of methods and apparatus for practicing those methods. The present embodiments can also be embodied in the form of program code embodied in tangible media, such as floppy diskettes, CD-ROMs, hard drives, or any other machine-readable storage medium, wherein, when the program code is loaded into and executed by a machine, such as a computer, the machine becomes an apparatus for practicing the embodiments. The present embodiments can also be in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the embodiments. When implemented on a general-purpose processor, the program code segments combine with the processor to provide a unique device that operates analogously to specific logic circuits.

The software is stored in a machine readable medium that may take many forms, including but not limited to, a tangible storage medium, a carrier wave medium or physical transmission medium. Non-volatile storage media include, for example, optical or magnetic disks, such as any of the storage devices in any computer(s) or the like. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: disks (e.g., hard, floppy, flexible) or any other magnetic medium, a CD-ROM, DVD or DVD-ROM, any other optical medium, any other physical storage medium, a RAM, a PROM and EPROM, a FLASH-EPROM, any other memory chip, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles of the embodiments and its practical applications, to thereby enable others skilled in the art to best utilize the various embodiments with various modifications as are suited to the particular use contemplated.

What is claimed is:

1. A method of capturing and analyzing luminescence images of a sample gemstone, the method comprising:

generating a first set of luminescence exciting beam pulses at a first light source;
directing the first luminescence exciting beam pulses through a first filter and to a first dichroic beam splitter, and a second dichroic beam splitter,
  wherein the first dichroic beam splitter is configured to reflect wavelengths of the first luminescence exciting beam pulses and pass wavelengths of luminescence excitation from the sample gemstone, and
wherein the second dichroic beam splitter is configured to pass wavelengths of the first luminescence exciting beam pulses;
receiving, at a camera with a computer processor and a memory, a first excited luminescence image from the sample gemstone on a stage, wherein the excited first luminescence image having passed through the first dichroic beam splitter and the second dichroic beam splitter;
receiving, at the camera with the computer processor and the memory, a second excited luminescence image from the sample gemstone on the stage, wherein the excited second luminescence image having passed through the second dichroic beam splitter and the first dichroic beam splitter and wherein the first and second excited luminescence image are captured by the camera 50 µs apart and responsive to triggers specifying a first time delay to capture the first excited luminescence image 130 µs after turning off the first luminescence exciting beam pulses;
digitizing, by the camera computer, the received first and second luminescence images of the sample gemstone; and
sending, by the camera computer, the digitized images of the sample gemstone to a computer data storage.

2. The method of claim 1 further comprising, generating a second set of luminescence exciting beam pulses at a second light source;
directing the second luminescence exciting beam pulses to the second dichroic beam splitter,
receiving, at the camera, a third excited luminescence image from the sample gemstone on a stage, wherein the excited third luminescence image having passed through the first dichroic beam splitter and the second dichroic beam splitter;
receiving, at the camera with a computer processor and a memory, a fourth excited luminescence image from the sample gemstone on a stage, wherein the excited fourth luminescence image having passed through the second dichroic beam splitter and the first dichroic beam splitter and wherein the third and fourth excited luminescence image are captured by the camera 50 µs apart and responsive to triggers specifying a second time delay to capture the third excited luminescence image 130 µs after turning off the second luminescence exciting beam pulses;
digitizing, by the camera computer, the received third and fourth luminescence images of the sample gemstone; and
sending, by the camera computer, the digitized images of the sample gemstone table to the computer data storage.

3. The method of claim 1 wherein the first light source are one of longwave UV light, shortwave UV light, or broadband UV light.

4. The method of claim 1 wherein the digitized images are one of, a white light image, and a fluorescence excited by longwave UV light.

5. The method of claim 2 wherein the digitized images are one of, a fluorescence excited by two different shortwave UV light, and a phosphorescence from UV light.

6. The method of claim 1 further comprising, analyzing, by a back end computer with a processor and a memory, the first and second stored digitized images for determination of whether the sample gemstone is a natural diamond, synthetic diamond, or not a diamond.

7. The method of claim 3 wherein the dichroic beam splitter is configured to reflect wavelengths of the first light source and pass wavelengths greater than 400 nm.

8. The method of claim 1 further comprising, determining by the computer, based on the digitized images, color, brightness, and decay of different luminescence features.

9. The method of claim 8 further comprising, determining by the computer, using on the digitized images, distinguishing natural diamonds from synthetic diamonds and diamond simulants based on color, brightness, and decay.

10. A system for gemstone analysis, comprising,
an optical layout with two light sources, wherein the light sources are both configured to illuminate a stage, wherein the two light sources are different wavelengths;
a top viewing camera in the optical layout configured to capture images of luminescence features in a gemstone under analysis on the stage,
wherein the camera is configured to view the stage through a first dichroic beam splitter where the first light source is aimed, and a second dichroic beam splitter where the second light source is aimed;
a computer in communication with the at least two light sources and camera, wherein the camera is configured to trigger the first light source on, trigger the first light source off, capture a first image about 130 μs after the first light source is triggered off, and capture a second image about 50 μs after the first image capture,
trigger the second light source on, trigger the second light source off, capture a third image about 130 μs after the second light source is triggered off, and capture a fourth image about 50 μs after the third image capture.

11. The system of claim 10 wherein the two different light sources are each at least one of a ultraviolet UV light emitting diode LED, laser, a laser driven light source LDLS, and a Xenon flash lamp.

12. The system of claim 10 wherein the digitized images are one of, a white light image, and a fluorescence excited by longwave UV light.

13. The system of claim 10 wherein the digitized images are one of a fluorescence excited by two different shortwave UV light, and a phosphorescence from UV light.

14. The system of claim 10 wherein the first light source and the second light source are each one of a longwave UV light, shortwave UV light, or broadband UV light.

15. The system of claim 10 wherein the computer is further configured, based on the digitized images, configured to define color, brightness, and decay of different luminescence features.

16. The system of claim 15 wherein the computer is further configured, to use the digitized images, to distinguish natural diamonds from synthetic diamonds and diamond simulants based on color, brightness, and decay.

17. A method for analyzing gemstones, the method comprising:
illuminating, by a first light source, a gemstone on a stage, wherein the first illumination is aimed at a first dichoric beam splitter, configured to reflect radiation from the first light source through a second dichroic beam splitter to the gemstone on the stage;
receiving, by a camera, aimed through the first dichroic beam splitter and the second dichoric beam splitter to the gemstone on the stage, a first set of images wherein the first set of images are captured at least 50 μs apart and are captured by the camera responsive to a first trigger specifying a first time delay to capture the first set of images at least 100 μs after turning off the first light source;
illuminating, by a second light source, the gemstone on a stage, wherein the second light source is aimed at a second dichroic beam splitter configured to reflect radiation from the second light source to the gemstone on the stage;
receiving, by the camera, aimed through the first dichroic beam splitter and the second dichoric beam splitter to the gemstone on the stage, a second set of images, wherein the second set of images are captured at least 50 μs apart and are captured by the camera responsive to a second trigger specifying a second time delay to capture the second set of images at least 100 μs after turning off the second light source.

18. The method of claim 17 wherein the first illumination is between 365 nm to 400 nm in wavelength.

19. The method of claim 17 wherein the first light source is an ultra-violet (UV) color light emitting diode (LED) with a band pass filter, and wherein the first set of images includes color and brightness of a gemstone fluorescence response under longwave UV light.

20. The method of claim 19 wherein the first set of images includes five images captured under illumination integration times between 0.5 ms and 200 ms.

21. The method of claim 17 wherein the second light source is a xenon flash lamp with a filter and wherein the second set of images includes color and brightness of a gemstone fluorescence response under shortwave UV light.

22. The method of claim 21 wherein the filter filters wavelengths of 227 nm or less.

23. The method of claim 21 wherein the second set of images includes three images captured under illumination integration times between 0.5 ms and 200 ms.

24. The method of claim 17 wherein the second light source is a xenon flash lamp with a 239 nm filter and wherein the second set of images includes color and brightness of a gemstone fluorescence response under another UV wavelength.

25. The method of claim 24 wherein the second set of images includes three images captured under illumination integration times of 50 ms, 200 ms, and 500 ms.

26. The method of claim 17 further comprising, illuminating, by the second light source, the gemstone on a stage, wherein the second light source is aimed at a second dichroic beam splitter configured to reflect radiation from the second light source to the gemstone on the stage;
receiving, by the camera, aimed through the first dichroic beam splitter and the second dichoric beam splitter to the gemstone on the stage, a third set of images.

27. The method of claim 26 wherein the second light source is a pulsing broad band xenon flash lamp and wherein the third set of images includes consecutively captured phosphorescence images of a gemstone under shortwave UV light.

28. The method of claim 17 wherein the camera is configured to capture images with 50 ms measurements.

* * * * *